(12) United States Patent
Izvozchikov et al.

(10) Patent No.: US 8,910,687 B2
(45) Date of Patent: Dec. 16, 2014

(54) DEVICE FOR PLACING HISTOLOGICAL AND BIOLOGICAL SAMPLES (75) Inventors: Ilya Borisovitch Izvozchikov, St. Petersburg (RU); Anatoliy Ivanovitch Kurapov, St. Petersburg (RU)

(73) Assignee: Ilya Borisovitch Izvozchikov, St. Petersburg (RU)

( * ) Notice: Subject to any disclaimer, the term of this patent is extended or adjusted under 35 U.S.C. 154(b) by 928 days.

(21) Appl. No.: 12/449,359

(22) PCT Filed: Feb. 1, 2008

(86) PCT No.: PCT/RU2008/000070
§ 371 (c)(1),
(2), (4) Date: Aug. 4, 2009

(87) PCT Pub. No.: WO2008/097137
PCT Pub. Date: Aug. 14, 2008

(65) Prior Publication Data
US 2010/0319181 A1 Dec. 23, 2010

(30) Foreign Application Priority Data
Feb. 9, 2007 (RU) ................................ 2007105906

(51) Int. Cl.
| B32B 37/02 | (2006.01) |
| B32B 37/14 | (2006.01) |
| B32B 41/00 | (2006.01) |
| G05G 15/02 | (2006.01) |
| G01N 1/31 | (2006.01) |
| G05G 15/06 | (2006.01) |
| G01N 35/00 | (2006.01) |

(52) U.S. Cl.
CPC ...... *G01N 1/312* (2013.01); *G01N 2035/00059* (2013.01); *G01N 2035/00049* (2013.01)
USPC ............................ 156/363; 156/521; 156/576

(58) Field of Classification Search
CPC .... B65C 9/16; B65C 9/105; B32B 17/10954; B32B 38/1841; B32B 38/1858; B44C 7/06; B65H 35/0033; B65H 37/005; A47C 9/027; A47C 16/04; G01N 1/312; G01N 2035/00059; G01N 2035/00049
USPC ................. 156/570, 571, 576, 363, 357, 521; 422/99
See application file for complete search history.

(56) References Cited

U.S. PATENT DOCUMENTS 4,319,542 A * 3/1982 Ojima et al. .................. 118/100
4,428,793 A 1/1984 Sato et al.
(Continued)

FOREIGN PATENT DOCUMENTS

DE 10144048 3/2003
RU 2148952 5/2000
(Continued)

*Primary Examiner* — Sonya Mazumdar
(74) *Attorney, Agent, or Firm* — Paul Vincent (57) ABSTRACT The device for placing histological and biological samples encompasses a working area, a bin for cover glasses with a slot in the lower part, a cover glass pusher embodied in the form of a plate, the thickness of which is less than the thickness of the cover glass, a unit for placing the cover glass, which can be reciprocally displaced above the working area, and a press connected to the drive for reciprocally displacing the cover glass placing unit. This unit is embodied in the form of at least one spring-loaded, narrow plate or needle, the length of which exceeds the width of the pusher, and situated directly under the cover glass pusher in the same fastener. Said fastener is connected to the reciprocating motion drive in a direction perpendicular to the working area, wherein the reciprocating motion drive is a carriage. The carriage also accommodates guides for lowering and lifting the press. The press is embodied in the form of at least one elastic clamping element secured to the arm. The arm has a side stop placed in contact with the carriage guides.

4 Claims, 6 Drawing Sheets

(56) References Cited

U.S. PATENT DOCUMENTS

| | | | |
|---|---|---|---|
| 5,356,595 A * | 10/1994 | Kanamori et al. | 422/65 |
| 5,580,414 A * | 12/1996 | Ljungmann | 156/363 |
| 5,989,386 A * | 11/1999 | Elliott | 156/707 |
| 6,302,985 B1 * | 10/2001 | Takahashi et al. | 156/99 |
| 6,382,693 B1 * | 5/2002 | Ljungmann | 294/188 |
| 6,474,386 B2 * | 11/2002 | Takahashi et al. | 156/362 |
| 6,521,186 B1 * | 2/2003 | Izvoztchikov et al. | 422/568 |
| 7,568,514 B2 * | 8/2009 | Izvoztchikov et al. | 156/571 |
| 7,748,423 B2 * | 7/2010 | Takahashi et al. | 156/350 |
| 2003/0047863 A1 * | 3/2003 | Lang et al. | 271/103 |

FOREIGN PATENT DOCUMENTS

| | | |
|---|---|---|
| WO | WO 9820379 A1 * | 5/1998 |
| WO | WO 2004/077051 | 9/2004 |
| WO | WO 2004077051 A1 * | 9/2004 |

* cited by examiner

DEVICE FOR PLACING HISTOLOGICAL AND BIOLOGICAL SAMPLES

This application is the national stage of PCT/RU2008/000070 filed on Feb. 1, 2008 and also claims Paris Convention priority to RU2007 105 906 filed on Feb. 9, 2007.

BACKGROUND OF THE INVENTION

The invention relates to medicine and biology, in particular to instruments for microscopic analyses and diagnoses, more precisely to devices for placing histological and biological samples in an optical medium for subsequent microscopic analysis.

Prepared and dyed histological and biological samples are accommodated (placed) in special media in order to create an optically uniform medium and preserve them for the time required for analysis. Various substances are used as the optical media, for example Canada balsam, Cedax or polystyrene. A drop (several drops) of a solution of one of the indicated substances in a suitable solvent is (are) applied to a sample located on the slide, and covered with a cover glass. After the solvent has dried, the samples placed in the optical medium can be preserved unchanged for several years.

Major laboratories specializing in histological and biological analyses in which hundreds of sections (samples) are processed every day use the highly productive devices.

The Consul device for placing samples from the English company Shandon (Shandon Consul. A versatile automatic coverslipper. Shandon Life Sciences Intern. Ltd. brochure) includes a cover glass storage bin with a pusher for laying out the cover glasses, a slide holder, optical medium solution metering dispenser, and a rolling unit.

The slide holder consists of half-frames secured to a rod and capable of rotating in a plane perpendicular to the rod. The rolling unit in the Consul device is comprised of a stage and two rollers, which are situated under the cover glass in the initial position. The stage and rollers are able to move perpendicularly to the plane of the cover glass, and the rollers are also capable of being deflected in conjunction with spring-loaded rockers.

The slides are mounted on a vertically placed bar. A swiveling device is used to move the slide to the working area. The cover glass storage device is mounted on a stand, just as the technological solution metering system.

The Consul device operates as follows:

Moving along a guide, the cover glass pusher shifts the lower glass from the storage bin to the working area. The dose of optical medium solution is dropped onto the cover glass from above. The swiveling device turns the half-frame with the slide around the rod, and delivers the slide into the working area, so that it comes to lie above the cover glass, sample down. The rolling unit stage lifts up, bringing the cover glass close to the slide. The rolling unit pusher continues to lift the rollers until they contact the cover glass, after which the spring-loaded rockers start to deflect, and the rollers roll on the surface of the cover glass. In this way, the central portion of the cover glass is compressed by the stage, while the rollers roll over the lateral portions. After this, the rolling unit descends, moves away from the slides, and the swiveling device returns the half-frame with placed slide to the initial position.

The Consul device makes it possible to place up to 400 samples an hour; the high productivity enables its successful use in laboratories specializing in pathohistological analyses.

The shortcoming to the Consul device is the horizontal arrangement of the cover glass and slide at the moment of pressing, which makes it more difficult to expel air pockets that form in the optical medium.

A device for placing samples according to U.S. Pat. No. 4,428,793, IPC[3] B65C 9/08, published on Jan. 31, 1984, includes a storage bin for cover glasses, a stage for arranging slides, and means for removing the cover glass from the storage bin, moving it to the stage where the slide is located, and lowering the cover glass onto the slide for placing the histological sample. This means consists of a holder, which accommodates a vacuum suction device and spring-loaded pusher, wherein the suction device is situated higher than the pusher. The device is vertically lowered into the storage bin for cover glasses in such a way that the suction device grips the cover glass; the pusher spring compresses in the process, and it ends up at the same level as the suction device. After the cover glass has been removed from the storage bin, the pusher spring is opened, releasing the edge of the cover glass. The means transfers the glass to the stage with slide at an angle to the horizontal created by the equally high position of the suction device and pusher. The means releases the cover glass with the lower end on the edge of the slide, which accommodates the drop or strip of medium to be placed. The pusher holds down the cover glass as the specified medium is lowered. The pusher spring is here compressed until the suction device and pusher are on the same horizontal, after which the vacuum suction device is removed from the cover glass. As a result, the cover glass is lowered onto the slide incrementally, at an angle, which facilitates the removal of air pockets from the medium.

One shortcoming to the known device is that the single cover glass, the thickness of which does not exceed 0.06-0.25 mm, is difficult to separate from the foot of the slides in the storage bunker, all the more so since the foot of the slides is compressed by the spring-loaded pusher during each separation using the specified device. In addition, gripping the cover glass with the spring-loaded pusher while placing it on the slide with the force necessary to compress the spring might result in damage to the histological sample.

A device for removing and placing cover glasses according to U.S. Pat. No. 5,989,386, IPC[6] B32 B31/04, published on Nov. 23, 1999, includes a head with one end accommodating two vacuum suction devices on planes situated at an angle relative to each other. Situated between the suction devices is a spring-loaded plunger, which is controlled by a solenoid and able to move up and down. When retracted, the plunger is unable to contact the cover glass. The head also encompasses a spring-loaded lever situated at the other end of the head, behind the suction device and plunger. The device operates as follows. The head is lowered into the storage bin with cover glasses until such time as the plunger contacts the uppermost glass, after which the suction device grips the uppermost glass. Exposed to the action of the plunger spring and angular orientation of the suction devices, the gripped cover glass bends and separates from the foot of the glass. The head transfers the cover glass to the slide. The opposing end of the cover glass gripped by the suction device is lowered with a lever, so that the cover glass lowers onto the slide at an angle to the horizontal. The head moves down until such time as the end of the cover glass gripped by the suction device comes to lie on the slide. The lever is secured to the head so as to move clockwise and counterclockwise, and places the cover glass on the slide, after which the suction device is detached.

The device according to U.S. Pat. No. 5,989,386 is intended to remove "a large percentage of free cover glasses", but practice has shown that vacuum suction devices are unable to separate one free glass at a time, and the cover glass has to be taken out of the bin with other implements, after which the glass can be gripped by means of the suction device. As in the device according to U.S. Pat. No. 4,428,793, using a spring-loaded plunger and lever in this device can end up damaging the histological sample.

A device for placing histological samples according to U.S. Pat. No. 6,474,386, IPC[7] B65 H29/24, published on Nov. 5, 2002, makes it possible to cautiously remove air from the space between the cover glass and slide. This device encompasses a platform for the slide and means for gripping and placing the glass on the slide at an inclination. The means for gripping and placing the cover glass include a cylinder mounted on the vertical stand, which is equipped with a motor and able to move up and down on the stand. The cylinder also incorporates a arm equipped with a separate motor, which is able to move clockwise and counterclockwise. A vacuum suction device joined with a vacuum pump is secured at the free end of the arm. The arm can lift the vacuum suction device and lower it to a level at which the gripped cover glass comes to lie horizontally.

The device according to U.S. Pat. No. 6,474,386 operates as follows.

A slide with histological sample and applied spot of medium are arranged on the platform for placement purposes. The gripping means use the suction device to grip one end of the cover glass and situated it above the slide in such a way that the gripped end comes to lie above the free end. The cylinder is then shifted down to a level where the horizontal axis where the arm is secured is lower than the slide situated on the platform. In this position, the lower end of the cover glass touches the edge of the slide at an acute angle to the horizontal. The arm is turned counterclockwise by a motor, and the cove glass held by the suction device is smoothly placed on the slide, after which the suction device is detached. It is stated that the device makes it possible to place the histological sample without damage.

One shortcoming to this device is that the cover glass has to be gripped with a vacuum suction device. This structural design requires a vacuum pump and quite complicated control, making the device heavier and more costly to manufacture.

The device for placing histological and biological samples [WO 2004/077051, IPC[7] G01N33/48, published on Sep. 10, 2004] includes a working area, cover glass bin with slot in the lower part of the bin, a cover glass pusher embodied in the form of a plate with a thickness less than the thickness of the cover glass, a unit for placing the cover glass, which can be reciprocally displaced above the working area, and a press connected to the drive for reciprocally displacing the cover glass placing unit. This device is designed like a comb; the working area (platform for holding the slide) is bordered from the placing means by way of a vertical stop with cuts, into which the teeth of the comb engage; the press is designed as a cylinder segment or spindle.

The device according to WO 2004/077051 operates as follows:

The cover glass with histological sample onto which the spot (strip) of medium is to be applied is accommodated in the working area for purposes of placement. The comb (placement means) is located above the slide, and the pusher moves the cover glass over it from the bin. The cover glass descends at an angle to the slide, incrementally moving the comb from the space between the cover glass and slide. As the comb moves, the press is actuated, pressing the cover glass against the slide.

The device according to WO 2004/077051 makes it possible to place histological samples without air pockets and damage to sample tissue, and does not require pneumatic and vacuum devices that hamper control. However, it is associated with the following shortcomings.

Access to the working area for cleaning and other servicing operations is impeded by the fact that the comb and press with transmission system are located above it. In order to service the working area, the entire assembly needs to be dismantled. In addition, since the cover glasses of different manufacturers differ somewhat in width, the vertical stop with cuts does not provide for the accurate arrangement of the cover glass on the slide. The glass "wanders", which makes it harder to continue working with the placed samples.

SUMMARY OF THE INVENTION

The object of the invention is to simplify the servicing of the instrument by facilitating access to the working area.

The object of the invention is also to increase the accuracy of arranging the cover glass on the slide.

The invention proposes a device for placing histological and biological samples, which encompasses a working area, a bin for cover glasses with a slot in the lower part, a cover glass pusher embodied in the form of a plate, the thickness of which is less than the thickness of the cover glass, a unit for placing the cover glass, which can be reciprocally displaced above the working area, and a press connected to the drive for reciprocally displacing the placing unit. The cover glass placing unit is embodied in the form of at least one spring-loaded, narrow plate or needle, the length of which exceeds the width of the pusher, and situated directly under the cover glass pusher in the same holder. The holder is connected to the reciprocating motion drive in a direction perpendicular to the working area. The reciprocating motion drive is a carriage, which also accommodates guides for lowering and lifting the press embodied in the form of at least one elastic clamping element secured to the arm. This arm has a side stop placed in contact with the carriage guides.

The cover glass placing unit can be embodied in the form of two or more spring-loaded, narrow plates or needles situated under the pusher in the same fastener.

The length of the narrow plate or needle must exceed the width of the pusher by more than a third of the width of the cover glass, but by no more than the width of the cover glass.

The working area can additionally accommodate a surface that protects the slide against excessive lowering.

The claimed device will be described with reference to the drawings shown on FIG. 1-10.

DESCRIPTION OF THE PREFERRED EMBODIMENT

A carriage 2 that acts as the reciprocal motion drive is situated by the casing wall 1 (FIG. 1-4) so that it can move horizontally along the walls 1. The carriage 2 is coupled with a holder 3, to which is secured the base of the cover glass pusher 4 and axis of rotation 5 for the cover glass placing unit embodied in the form of a narrow plate or needle 6. The upper surface of the plate or needle 6 contacts the lower surface of the pusher 4; the length of the plate or needle 6 is greater than the width of the pusher 4 by at least one-third the width of the cover glass. The plate or needle 6 is loaded by spring 7. The cover glasses 8 are located in the cover glass bin 9. The slide 10 with histological sample is arranged in the working area of the dive, which incorporates a protective surface 11 embodied in the form of parallel rods, eyelets or lattices. The press consists of elastic compression element(s) 12 located on arm 13, and has a side stop 14; the arm is mounted so that it can turn on the casing wall 1 via holder 15. The press can include 1-3 elastic compression elements 12; if there are more than one compression elements, they are secured to the plate in a row. The side stop 14 reaches the surface of the carriage 2. The carriage 2 accommodates guides 16 embodied in the form of two curvilinear surfaces. The guides 16 are situated on the carriage 2 with a gap, and joined via the spring-loaded plate 17. In the idle state, the stop 14 of the press is located at the height of the guides 16 (see FIG. 6).

The cover glass placing unit can be embodied in the form of a single narrow plate or needle; however, there can be more than one narrow plate or needle. In the latter case, several narrow plates or needles must be situated on the rotational axis 5 and loaded spring 7.

The device operates as follows.

Figure 1:
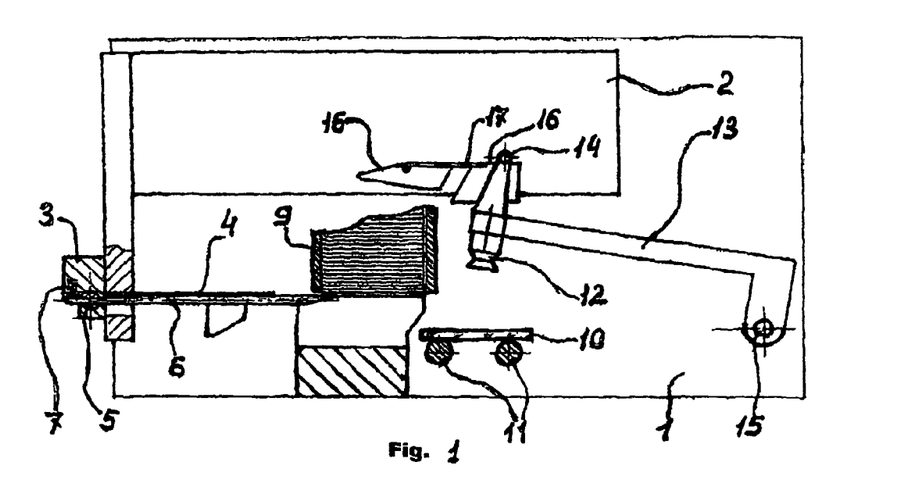
FIG. 1 presents the claimed device.
Figure 2:
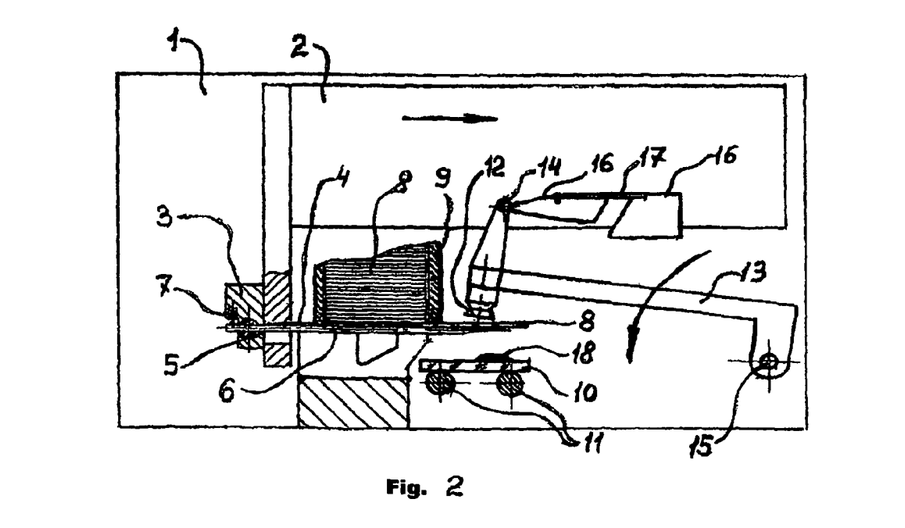
FIG. 2-4 present the claimed device in the process of placing the samples.
Figure 3:
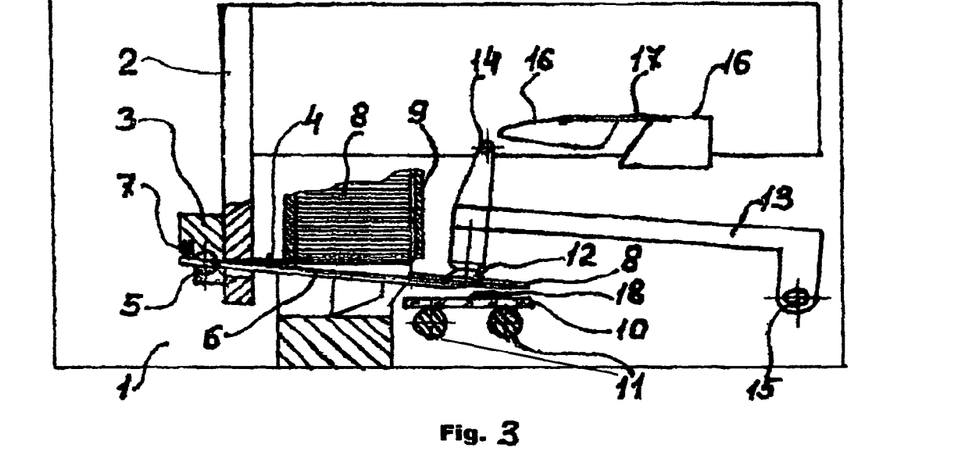
Figure 4:
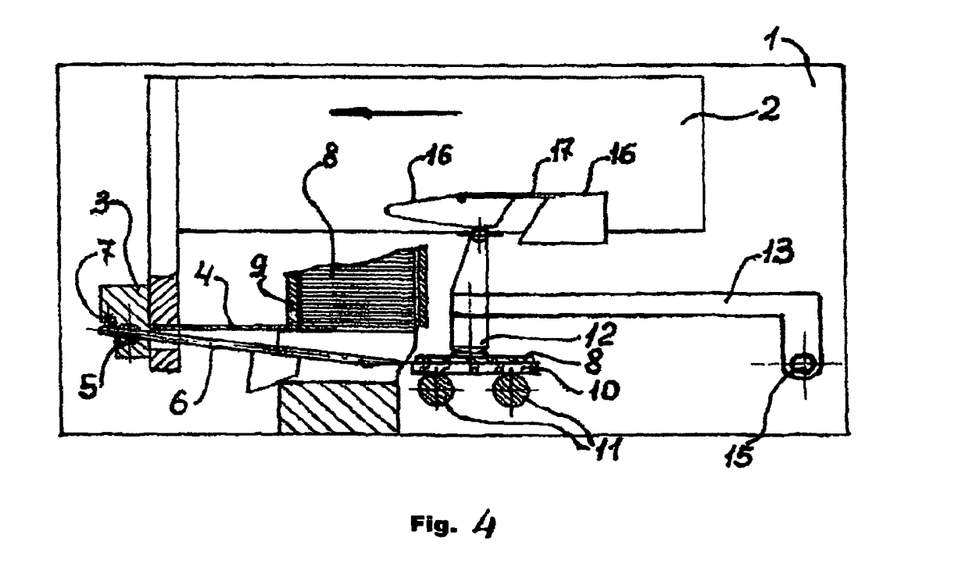
Figure 5:
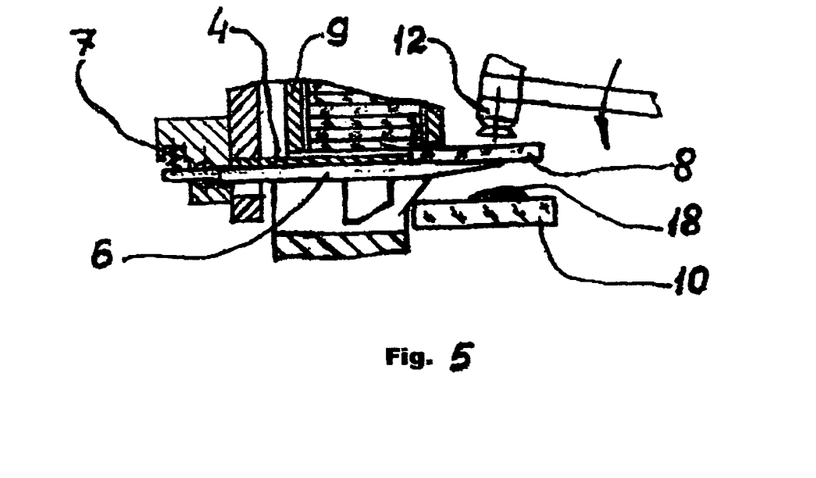
FIG. 5 presents an enlarged image of the placing unit at the moment the cover glass exits the bin (same as position in FIG. 2).
Figure 5A:
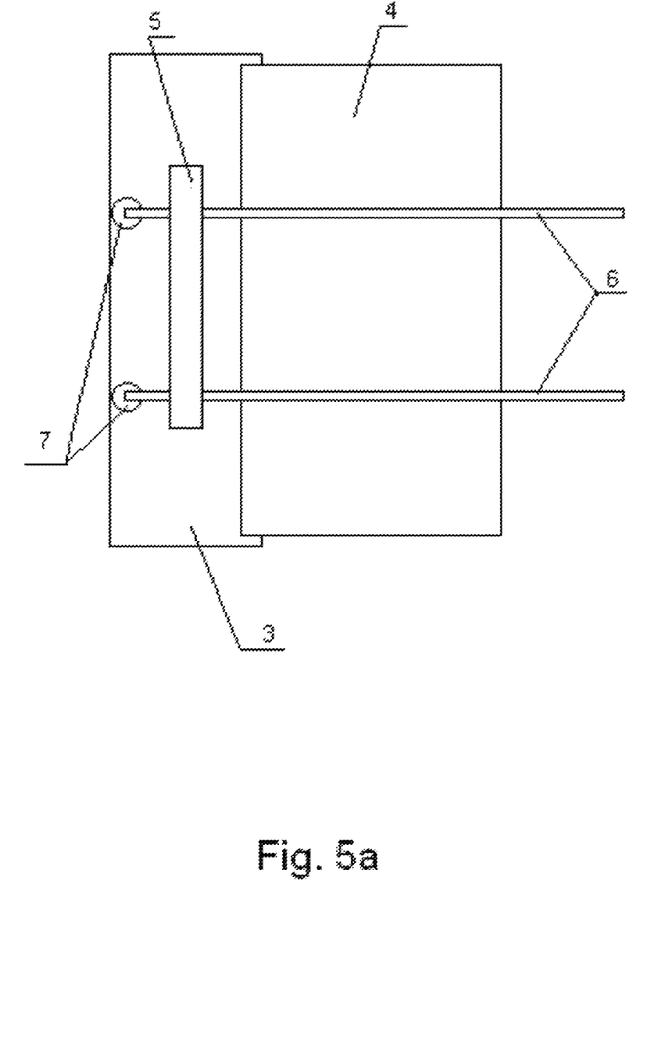
FIG. 5a shows an embodiment of the invention in which the placing unit comprises two spring-loaded plates or needles
Figure 6:
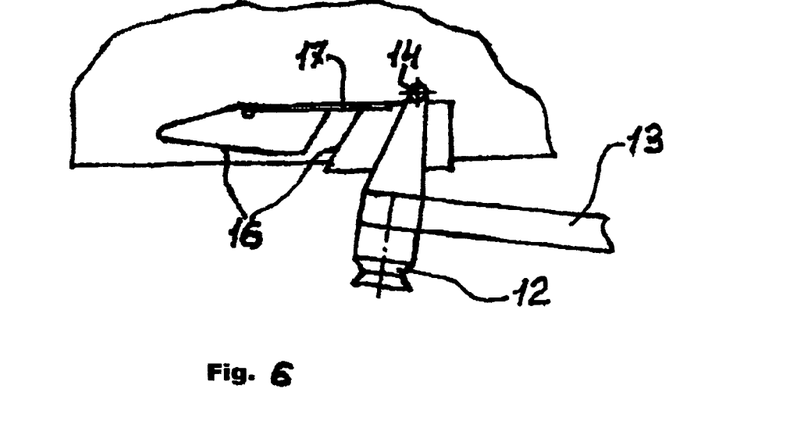
FIG. 6-10 present the movement of the press stop along the guide with the device in operation.
Figure 7:
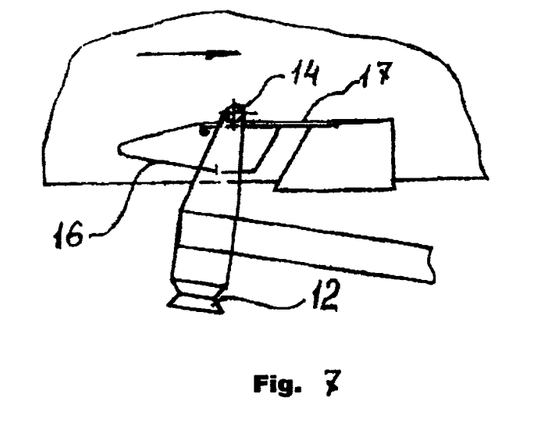
Figure 8:
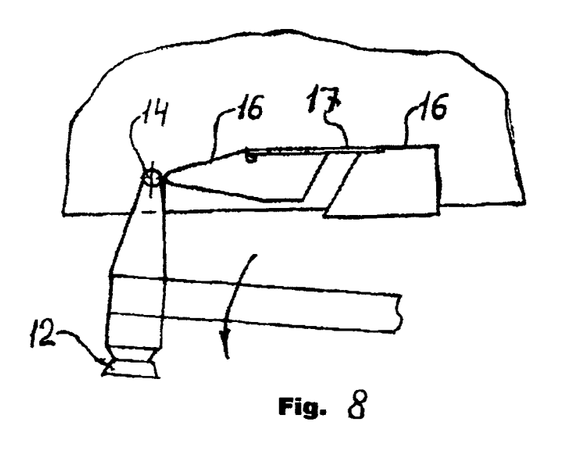
Figure 9:
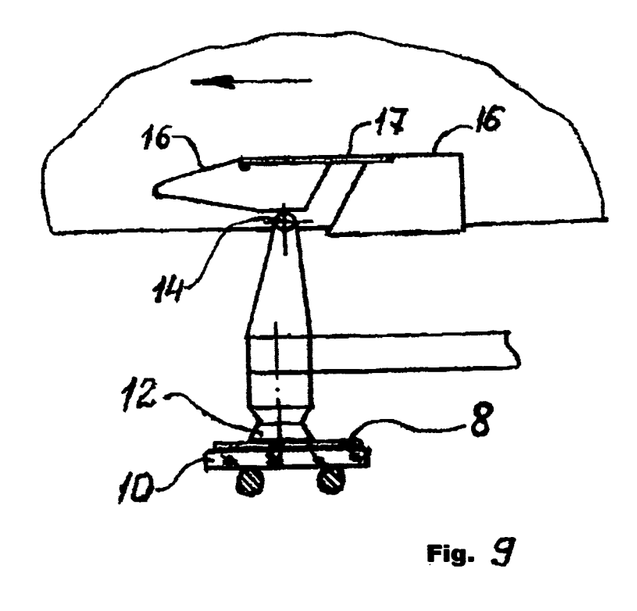
Figure 10:
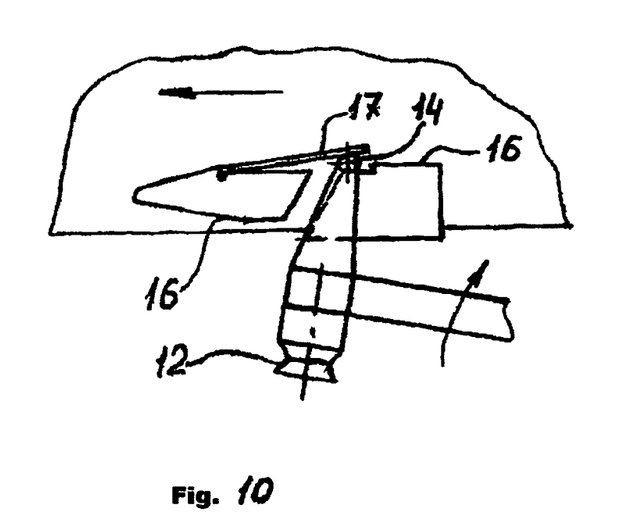

A slide 10 is situated inside the working area. At the same time, a finishing medium (e.g., solution of polystyrene in xylene) is applied from a metering dispenser (not shown) to the slide 10 (see FIG. 2). As the carriage 2 moves to the right, the pusher 4 moves the cover glass 8 from the bin 9 on the narrow plate or needle 6 in the way shown on FIG. 5. The cover glass 8 is here fixed in this position from below by the spring-loaded plate or needle 6, and from above by the edge of the wall of the bin 9, and comes to be situated directly above the slide. As the carriage 2 moves to the right, the stop 14 of the press simultaneously slides along the guides 16 above the plate 17 (FIG. 7) and, falling from the guides 16, allows the press to lower onto the cover glass (FIGS. 2 and 8). The weight of the released press deflects the cover glass 8 as the plate or needle 6 drops, which is loaded by the spring 7 and rotates around axis 5 (FIG. 3). The cover glass 8 is lowered on the slide 10 at an angle relative to the strip 18 of the medium for placement. After touching the cover glass and slide, the carriage 2 moves to the left, and plate or needle 6 exits form under the cover glass (FIGS. 4 and 9), and is then returned to the initial position by the spring 7. After the plate or needle 6 have exited, the cover glass rests on the slide. The movement of the carriage 2 forces the stop 14 to return through the gap between the guiding surfaces 16, lifting the spring-loaded plate 17 (FIG. 10) into the initial position, as shown on FIG. 6.

The operation of the claimed device can be automated. The entire placing cycle takes 7-9 seconds.

The instrument is easy to service, the working area is accessible by tilting the press arm on the holder 15 to the side (right). The pusher 4 and placing unit 6 are situated together as depicted in the description on the drawings, making it possible to monitor the position of the cover glass and accurately place it on the slide.

The claimed device for placing histological and biological samples can be used in laboratories specializing in histological analyses, and also in any other biological and medical institutions involved in microscopic analyses of cells and tissue.

We claim:

1. A device for cover slipping histological and biological samples deposited on slides and supplied to the device at a working area, the device applying cover glasses to the slides, thereby covering the histological and biological samples, the device comprising:
    a casing;
    a bin for cover glasses, said bin mounted to said casing, said bin having a slot in a lower part thereof, wherein said bin is disposed, structured and dimensioned to facilitate placement of the cover glasses onto the slides at the working area;
    a reciprocating motion drive having a carriage movably mounted to said casing for transverse displacement relative to said casing and above the working area;
    a holder mounted to said carriage;
    a cover glass pusher mounted to said holder, said cover glass pusher having a thickness which is less than a thickness of a cover glass, said pusher also having a width;
    at least one spring-loaded plate or needle mounted to said holder for rotation about a horizontal axis, said plate or needle having a length which exceeds said width of said pusher, wherein said pusher and said plate or needle move together and along with said carriage during transverse displacement of said carriage, thereby permitting reciprocal displacement of said plate or needle between a resting position outside the working area and a working position above the working area;
    a curved guide mounted to said carriage; and
    a press mounted separately to said casing for rotation about a horizontal axis, said press having an arm carrying at least one elastic pressing element and supporting a side stop, said side stop being disposed, structured and dimensioned for guidance by said curved guide during transverse displacement of said carriage to raise and lower said arm over the working area during reciprocal transverse movement of said carriage relative to said casing.

2. The device of claim 1, wherein said at least one plate or needle comprises two spring-loaded plates or needles.

3. The device of claim 1, wherein said length of said at least one spring-loaded plate or needle exceeds said width of said cover glass pusher by more than one third of a cover glass width.

4. The device of claim 1, further comprising a protective surface for a slide in the working area.

* * * * *